United States Patent [19]

Spitzer et al.

[11] 4,368,156
[45] Jan. 11, 1983

[54] PREPARATION OF 4-HALOAZETIDIN-2-ONES FROM 4-SULFINOAZETIDIN-2-ONES

[75] Inventors: Wayne A. Spitzer, Indianapolis; Stjepan Kukolja, Carmel; Theodore Goodson, Jr., Indianapolis, all of Ind.; Steven R. Lammert, Decatur, Ill.

[73] Assignee: Eli Lilly and Company, Indianapolis, Ind.

[21] Appl. No.: 241,872

[22] Filed: Mar. 9, 1981

[51] Int. Cl.$^3$ .................... C07D 205/08; C07B 9/00; C07D 403/04; C07D 401/04
[52] U.S. Cl. .................... 260/239 A; 260/239.3 R; 260/245.4; 260/330.3; 546/208; 260/330.9
[58] Field of Search ...... 260/239 AL, 245.4, 239.3 R, 260/330.3; 546/208

[56] References Cited

U.S. PATENT DOCUMENTS

| | | | |
|---|---|---|---|
| 4,013,653 | 3/1977 | Wolfe | 260/244 R |
| 4,081,440 | 3/1979 | Kukolja | 260/239 A |
| 4,138,486 | 2/1979 | Narisada et al. | 424/248.52 |
| 4,159,266 | 6/1979 | Kukolja | 260/239 A |

OTHER PUBLICATIONS

Campbell, J.C.S. Perkins I, p. 1208, (1975).

Primary Examiner—Mark L. Berch
Attorney, Agent, or Firm—William B. Scanlon; Arthur R. Whale

[57] ABSTRACT

Process for 4-halo azetidinones of the formula

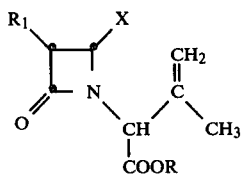

wherein $R_1$ is acylamino or diacylamino, X is chloro, bromo or iodo, and R is a carboxy-protecting group which comprises treating a 4-sulfinoazetidinone of the formula

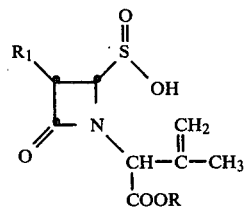

with positive halogen reagent, eg. N-chlorosuccinimide, N-bromosuccinimide, N-iodosuccinimide, hypohalite. The 4-haloazetidinones are useful intermediate for β-lactam antibiotics.

21 Claims, No Drawings

PREPARATION OF 4-HALOAZETIDIN-2-ONES FROM 4-SULFINOAZETIDIN-2-ONES

BACKGROUND OF THE INVENTION

This invention relates to a process for preparing 3-acylamido or 3-diacylamido-4-haloazetidin-2-ones represented by the following general formula

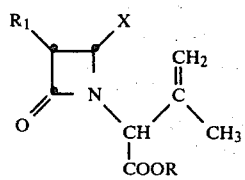

wherein X is chloro, bromo or iodo; $R_1$ is an acylamido or diacylamido group having either the natural $\beta$-configuration or the epi($\alpha$-) configuration; and R is a carboxy-protecting group.

The 4-haloazetidinones provided by the process of this invention are useful intermediates in the preparation of $\beta$-lactam antibiotics. For example, S. Wolfe, U.S. Pat. Nos. 3,948,927, 3,950,352, 4,013,653, and 4,071,512, teaches the use of 4-haloazetidinones in the preparation of the so-called 1-oxapenicillins and the corresponding 1-oxa(dethia)cephalosporins. S. Wolfe, *Canadian Journal of Chemistry*, 52, 3996–3999 (1974) teaches the same use for the 4-haloazetidinones. Further, Narisada, *Heterocycles*, Vol. 7, No. 2 (1977) pp. 839–849 reports the preparation of 1-oxa-$\beta$-lactam antibiotics with 4-haloazetidinones.

The usefulness and general versatility of the 4-haloazetidinones as intermediates for $\beta$-lactam antibiotics has prompted research directed to alternative methods for their preparation from readily available and economic starting material.

SUMMARY OF THE INVENTION

This invention provides a process for the preparation of 4-haloazetidinones represented by the above general formula which comprises reacting in an inert solvent an azetidin-2-one-4-sulfinic acid represented by the formula

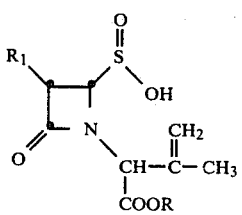

with a positive halogen, X+, reagent. In the above formula, $R_1$ and R have the same meanings as described in the foregoing formula of the 4-haloazetidinones. Positive halogen reagents refer to halo compounds known to provide positive halogen, e.g. Cl+, Br+, and I+ such as the N-haloamides and N-haloimides.

DETAILED DESCRIPTION

According to the process of this invention an azetidin-2-one-4-sulfinic acid represented by the formula 1

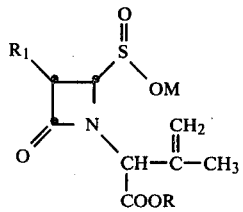

is reacted in an inert organic solvent at a temperature between about −20° C. and about 45° C. with at least a molar equivalent of positive halogen reagent to provide a 4-haloazetidinone represented by the formula 2.

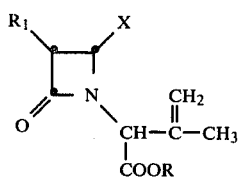

In the above formulas 1 and 2 $R_1$ is
(1) an imido group of the formula

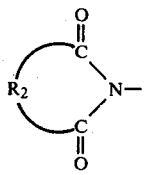

wherein $R_2$ is $C_2$–$C_4$ alkylene or 1,2-phenylene;
(2) an amido group of the formula

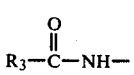

wherein $R_3$ is
(a) hydrogen, $C_1$–$C_4$ alkyl, halomethyl, cyanomethyl, benzyloxy, p-nitrobenzyloxy, t-butyloxy, 2,2,2-trichloroethoxy, or p-methoxybenzyloxy;
(b) the group R', wherein R' is phenyl or phenyl substituted by 1 or 2 halogens, protected hydroxy, nitro, cyano, $C_1$–$C_4$ alkyl, or $C_1$–$C_4$ alkoxy;
(c) a group of the formula

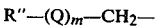

wherein R" is R' as defined above, 1,4-cyclohexadienyl, thienyl or furyl; m is 0 or 1; and Q is 0; with the limitation that when m is 1, R" is R';
(d) a group of the formula

wherein R" is as defined above, and W is protected hydroxy, protected carboxy, or protected amino;
(3) an imidazolidinyl group of the formula

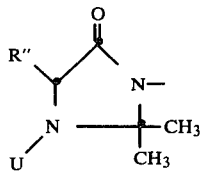

wherein R" is as defined above and U is nitroso or acetyl; or $R_1$ is (4) an imido group of the formula

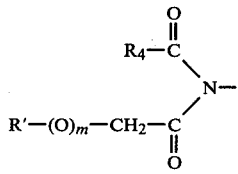

wherein R' is as defined above, m is 0 or 1, and $R_4$ is $C_1$–$C_4$ alkyl, $C_1$–$C_4$ haloalkyl, $C_1$–$C_4$ alkoxy, or 2,2,2-trichloroethoxy;

and R is a carboxy-protecting group. In the formula 2, X is chloro, bromo or iodo. M in the formula 1 is hydrogen, sodium or potassium.

In the above definition of the starting materials and products of the process, the term "$C_1$–$C_4$ alkyl" refers to methyl, ethyl, n-propyl, iso-propyl, n-butyl, sec-butyl, and t-butyl; "$C_1$–$C_4$ alkoxy" refers to methoxy, ethoxy, n-propoxy, iso-propoxy, n-butoxy, and t-butoxy; "halogen" refers to fluoro, chloro, or bromo; while the terms "protected hydroxy," "protected amino" and "protected carboxy" refer to the hydroxy, amino, and carboxy groups substituted with a conventional blocking group used for the temporary protection of the hydroxy, amino or carboxy group.

Illustrative of the particular acylamino group,

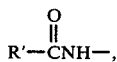

are benzamido, 2,6-dimethoxybenzamido, 4-chlorobenzamido, 4-methylbenzamido, 3,4-dichlorobenzamido, 4-cyanobenzamido, 3-bromobenzamido, 3-nitrobenzamido and the like.

Exemplary of the acylamino group

when $R_3$ is a group of the formula R"—(Q)$_m$CH$_2$— and m is 0, are cyclohexa-1,4-dienylacetamido, phenylacetamido, 4-chlorophenylacetamido, 3-methoxyphenylacetamido, 3-cyanophenylacetamido, 3-methylphenylacetamido, 4-bromophenylacetamido, 4-ethoxyphenylacetamido, 4-nitrophenylacetamido, 3,4-dimethoxyphenylacetamido, 2-thienylacetamido, 3-thienylacetamido and the like; and when m is 1 and Q is 0, representative acylamino groups are phenoxyacetamido, 4-cyanophenoxyacetamido, 4-chlorophenoxyacetamido, 3,4-dichlorophenoxyacetamido, 2-chlorophenoxyacetamido, 4-methoxyphenoxyacetamido, 2-ethoxyphenoxyacetamido, 3,4-dimethylphenoxyacetamido, 4-isopropylphenoxyacetamido, 3-cyanophenoxyacetamido, 3-nitrophenoxyacetamido and like substituted phenoxyacetamido groups.

Illustrative of the acylamino groups when $R_3$ is a substituted arylalkyl group of the formula

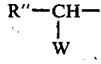

and when W is protected hydroxy are 2-formyloxy-2-phenylacetamido, 2-benzyloxy-2-(4-methoxyphenyl)-acetamido, 2-(4-nitrobenzyloxy)-2-(3-chlorophenyl)-acetamido, 2-chloroacetoxy-2-(4-methoxyphenyl)-acetamido, 2-benzyloxy-2-phenylacetamido, 2-trimethylsilyloxy-2-(4-chlorophenyl)acetamido, 2-benzhydryloxy-2-phenylacetamido and like groups. Representative of such groups when W is protected amino are 2-(4-nitrobenzyloxycarbonylamino)-2-phenylacetamido, 2-(2,2,2-trichloroethoxycarbonylamino)-2-phenylacetamido, 2-chloroacetamido-2-(1,4-cyclohexadien-1-yl)acetamido, 2-(4-methoxybenzyloxycarbonylamino)-2-(4-methoxyphenyl)-acetamido, 2-benzhydryloxycarbonylamino-2-phenylacetamido, 2-(1-carbomethoxy-2-propenyl)amino-2-phenylacetamido, 2-(4-nitrobenzyloxycarbonylamino)-2-(2-thienyl)acetamido, and like groups. Representative of such groups when W is protected carboxy are 2-(4-methoxybenzyloxycarbonyl)-2-phenylacetamido, 2-benzyloxycarbonyl-2-phenylacetamido, 2-diphenylmethyloxycarbonyl-2-phenylacetamido, 2-(4-nitrobenzyloxycarbonyl)-2-phenylacetamido, 2-(2,2,2-trichloroethoxycarbonyl)-2-(2-thienyl)acetamido, 2-(4-methoxybenzyloxycarbonyl)-2-(4-tetrahydropyran-2-ylphenyl)acetamido, and like groups.

Representative of $R_1$ when $R_1$ is an imido group of the formula

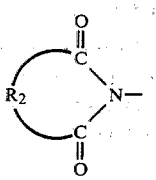

are phthalimido, succinimido, and glutarimido.

Exemplary groups represented by $R_1$ when $R_1$ is an imido group of the formula

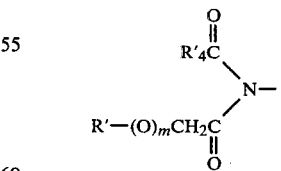

are N-acetyl-N-phenylacetylamino, N-trichloroethoxycarbonyl-N-phenoxyacetylamino, N-propoxycarbonyl-N-(4-chlorophenoxy)acetylamino, N-(2-bromoacetyl)-N-phenoxyacetylamino, and like acyclic imido groups.

Representative of $R_1$ when $R_1$ is an imidazolidinyl group of the formula

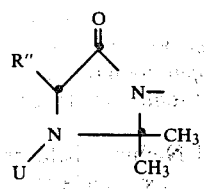

are the 2,2-dimethyl-3-nitroso-5-oxo-4-phenyl-1-imidazolidinyl group, the 2,2-dimethyl-3-nitroso-5-oxo-4-(4-benzyloxyphenyl)-1-imidazolidinyl group, the 2,2-dimethyl-3-acetyl-5-oxo-4-(1,4-cyclohexadien-1-yl)-1-imidazolidinyl group, the 2,2-dimethyl-3-nitroso-5-oxo-4-(2-thienyl)-1-imidazolidinyl group and like substituted imidazolidinyl groups.

The term R in the formulas 1 and 2 represents a conventional carboxy-protecting ester group, for example, those ester groups commonly used to protect carboxylic acid functions in the penicillin and cephalosporin art. Illustrative of such groups are the alkyl and substituted alkyl ester groups such as t-butyl, 2,2,2-trichloroethyl, 2,2,2-tribromoethyl, 2-iodoethyl, phthalimidomethyl, and the like; the arylalkyl groups such as benzyl, p-nitrobenzyl, p-methoxybenzyl, diphenylmethyl, 4-methoxydiphenylmethyl, methylbenzyl, 3,5-dihydroxybenzyl, and the like. Such esters are employed in this process to prevent the untoward reaction of the carboxylic acid function with the positive halogen reagent. They also aid in the isolation of the 4-haloazetidinones and lend crystallinity to the products.

Examples of amino-protecting groups which can be used in the process to likewise block the free amino function include the conventional amino protecting groups such as those forming urethanes with the amino group eg., t-butyloxycarbonyl, cyclopentyloxycarbonyl, 2,2,2-trichloroethoxycarbonyl, benzyloxycarbonyl, p-nitrobenzyloxycarbonyl, diphenylmethoxycarbonyl, and the like; those forming enamines with β-dicarbonyl compounds eg., methyl acetoacetate and ethyl acetoacetate; and other groups such as the trityl group.

Hydroxy-protecting groups which are conventional and are useful in the process include the halo ester type such as chloroacetyl, trichloroacetyl, dichloroacetyl and bromoacetyl; the ethers such as tetrahydropyranyl, 1-ethoxyethoxy (obtained on protection of the hydroxy group with ethyl vinyl ether), and the like; the silyl groups eg., trialkylsilyl groups such as trimethylsilyl, triethylsilyl, etc.

Other carboxy, amino and hydroxy-protecting groups are well known for example, those described in Chapters, 2, 3, and 5, "*Protecting Groups In Organic Chemistry,*" J. F. W. McOmie, Ed., Plenum Press, New York N.Y. 1973.

As mentioned above, the process of this invention comprises reacting an azetidinone-4-sulfinic acid of the formula 1 with at least a molar equivalent of a positive halogen selected from Cl+, Br+, and I+. In carrying out the process, the positive halogen is generated in situ with a positive halogen reagent which is capable of delivering a positively charged halogen. In general, such reagents comprise a halogen atom bonded directly to nitrogen or to oxygen in the molecule. Likewise molecular halogen, ie. $Cl_2$, $Br_2$ and $I_2$, may be used as a positive halogen reagent since by dissociation, $Cl_2 \rightleftharpoons Cl^+ + Cl^-$, $Cl^+$ is generated. The N-chloro reagents for positive chlorine employed in the process are represented by the following formula

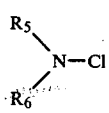

in which $R_5$ is hydrogen, chloro, $C_1$–$C_3$ alkyl, cyclohexyl, phenyl, or phenyl substituted with chloro, bromo, methyl, or nitro, and $R_6$ is $R_7$—X— in which $R_7$ is $C_1$–$C_3$ alkyl, cyclohexyl, phenyl or phenyl substituted with chloro, bromo, methyl, or nitro, and X is

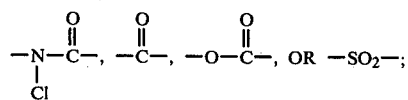

or $R_5$ and $R_6$ taken together with the nitrogen to which they are bonded define a heterocyclic structure of the formula

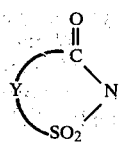

in which Y is o-phenylene, or —$(CH_2)_n$— in which n is 2 or 3; or a structure of the formula

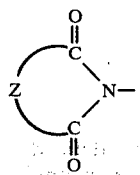

in which Z is Y as hereinbefore defined or a group of the formula

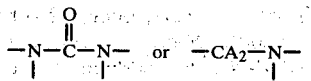

in which A is hydrogen or methyl.

Several types of preferred N-chloro compounds which can be employed are described by the above definition. These N-chloro compounds include (a) ureas, (b) amides, (c) urethans, (d) sulfonamides, (e) sulfimides, (f) imides, (g) hydantoins, and (h) isocyanuric acids.

The preferred N-chloro ureas which can be employed in this invention generally have the formula

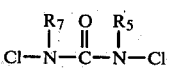

in which $R_5$ is hydrogen, chloro, $C_1$–$C_3$ alkyl, cyclohexyl, phenyl, or phenyl substituted with chloro, bromo, methyl, or nitro, and $R_7$ is $C_1$–$C_3$ alkyl, cyclohexyl, phenyl, or phenyl substituted with chloro, bromo, methyl, or nitro.

Illustrative of these ureas are
N,N'-dichloro-N-methylurea;

N,N'-dichloro-N-ethyl-N'-cyclohexylurea;
N,N'-dichloro-N-phenylurea;
N,N'-dichloro-N,N'-diphenylurea;
N,N'-dichloro-N-(p-tolyl)urea;
N,N'-dichloro-N-(m-chlorophenyl)-N'-methylurea;
N,N'-dichloro-N,N'-dicyclohexylurea;
N,N'-dichloro-N-isopropyl-N'-(p-tolyl)urea;
N,N'-dichloro-N-phenyl-N'-propylurea;
N,N'-dichloro-N-cyclohexyl-N'-(p-nitrophenyl)urea;
N,N,N'-trichloro-N-methylurea;
N,N,N'-trichloro-N-phenylurea; and the like.

The preferred N-chloro amides which can be employed in this invention generally have the formula

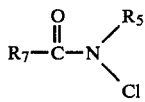

in which $R_5$ and $R_7$ are as hereinbefore defined.

Illustrative of these amides are N-chloroacetamide, N-chloropropionamide, N-chloro-N-methylacetamide, N,N-dichloroacetamide, N-chloro-N-cyclohexylacetamide, N-chloro-N-ethylbenzamide, N-chloro-p-chlorobenzamide, N-chloro-p-toluamide, N-chloro-N-phenylpropionamide, N-chloro-N-(m-bromophenyl)-butyramide, N-chlorohexahydrobenzamide, N,2,4-trichloroacetanilide, and the like.

The preferred N-chloro urethans which can be used in accordance with this invention generally have the formula

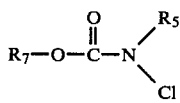

in which $R_5$ and $R_7$ are as hereinbefore defined.

Illustrative of these urethans are methyl N,N-dichlorocarbamate, ethyl N,N-dichlorocarbamate, phenyl N,N-dichlorocarbamate, cyclohexyl N,N-dichlorocarbamate, methyl N-chlorocarbamate, ethyl N-chlorocarbamate, ethyl N-cyclohexyl-N-chlorocarbamate, phenyl N-chlorocarbamate, phenyl N-phenyl-N-chlorocarbamate, p-tolyl N-chlorocarbamate, m-chlorophenyl N-methyl-N-chlorocarbamate, cyclohexyl N-cyclohexyl-N-chlorocarbamate, isopropyl N-p-tolyl-N-chlorocarbamate, phenyl N-propyl-N-chlorocarbamate, cyclohexyl N-p-nitrophenyl-N-chlorocarbamate, and the like.

The preferred N-chloro sulfonamides which can be used in accordance with this invention have the formula

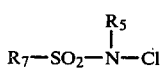

in which $R_5$ and $R_7$ are as hereinbefore defined.

Illustrative of the sulfonamides which can be employed as halogenating agents are N,N-dichlorobenzenesulfonamide, N,N-dichloromethanesulfonamide, N,N-dichlorocyclohexanesulfonamide, N,N-dichloro-p-toluenesulfonamide, N-chloromethanesulfonamide, N-cyclohexyl-N-chlorobenzenesulfonamide, N-cyclohexyl-N-chloroethanesulfonamide, N-chlorobenzenesulfonamide, N-phenyl-N-chlorobenzenesulfonamide, N-chloro-p-toluenesulfonamide, N-ethyl-N-chloro-m-nitrobenzenesulfonamide, N-methyl-N-chloro-m-chlorobenzenesulfonamide, N-methyl-N-chloro-p-toluenesulfonamide, N-cyclohexyl-N-chlorocyclohexanesulfonamide, N-p-tolyl-N-chloroisopropanesulfonamide, N-propyl-N-chlorobenzenesulfonamide, N-p-nitrophenyl-N-chlorocyclohexanesulfonamide, and the like.

A further preferred type of N-chloro halogenating agent which can be employed is a sulfimide of the formula

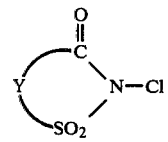

in which Y is o-phenylene, —CH$_2$—CH$_2$—, or —CH$_2$—CH$_2$—CH$_2$—. These compounds include o-sulfobenzoic N-chloroimide, β-sulfopropionic N-chloroimide, and γ-sulfobutyric N-chloroimide.

Also preferred for use as N-chlorohalogenating agents in accordance with this invention are N-chloroimides of the formula

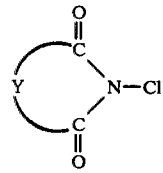

in which Y is o-phenylene, —CH$_2$—CH$_2$—, or —CH$_2$—CH$_2$—CH$_2$—. These compounds include N-chlorophthalimide, N-chlorosuccinimide, and N-chloroglutarimide.

N,N-Dichlorohydantoins can also be employed as halogenating agents in accordance with this invention. These hydantoins have the formula

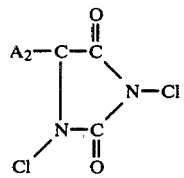

in which A is hydrogen or methyl, and include 1,3-dichlorohydantoin, 1,3-dichloro-5-methylhydantoin, and 1,3-dichloro-5,5-dimethylhydantoin.

Another type of halogenating agent which can be employed is a class of isocyanuric acids which includes N,N',N''-trichloroisocyanuric acid having the formula

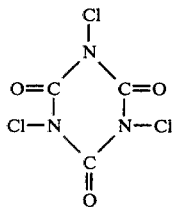

Many of the N-chloro halogenating agents employed in the process of this invention are available commercially, and any of them can be prepared by methods well recognized throughout the chemical arts. Typical of the literature sources which detail preparation of the N-chloro halogenating agents are Bachand et al., J. Org. Chem. 39, (1974) pp. 3136–3138; Theilacker et al., Liebigs Ann. Chem. 703, (1967) pp. 34–36; and Houben-Weyl, *Methoden der Organischen Chemie,* Volume V/3, pp. 796–810.

N-Chloro halogenating agents which are highly preferred for use in the process of this invention are N-chloroimides, and particularly N-chlorosuccinimide or N-chlorophthalimide.

The O-chloro reagents which can be used in the process as sources of positive chlorine are preferably compounds of the formula M—O—Cl wherein M is sodium, potassium, calcium, t-butyl or t-amyl. Examples of such O-chloro compounds are sodium, potassium or calcium hypochlorite, and tertiary-butyl hypochlorite and tertiary-amyl hypochlorite.

The N-bromo reagents used as sources of positive bromine in the process are represented by the formula

wherein $R_8$ is hydrogen, $C_2$-$C_6$ alkanoyl, $C_2$-$C_6$ haloalkanoyl, or benzenesulfonyl; or $R_8$ and $R_9$ taken together with the nitrogen atom to which they are attached form a cyclic group of the formula

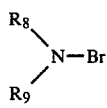

wherein Y has the same meanings as defined above with respect to the N-chloro reagents; or a cyclic group of the formula

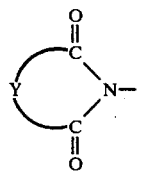

wherein Y has the same meanings defined hereinbefore.

Examples of the N-bromo reagents which can be employed as sources of positive bromine are listed below.

N-Bromoacetamide(NBA),CH₃CONHBr
N-Bromo(chloroacetamide),ClCH₂CONHBr
N-Bromo(trifluoroacetamide),F₃CCONHBr
N-Bromourethane,C₂H₅OCONHBr
N-Bromocarbamide,H₂NCONHBr
N-Bromoacetanilide,CH₃CON(Br)C₆H₅
N-Bromobenzamide,C₆H₅CONHBr
N-Bromodiacetamide,(CH₃CO)₂NBr
N-Bromobenzenesulphonamide,C₆H₅SO₂NHBr
N,N-Dibromobenzenesulphonamide,C₆H₅SO₂NBr₂

Isocyanuric bromide 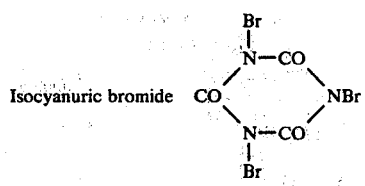

N—Bromocaprolactam, (CH₂)₅ 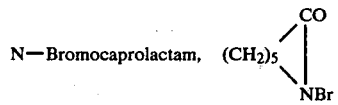

N—Bromosaccharin, 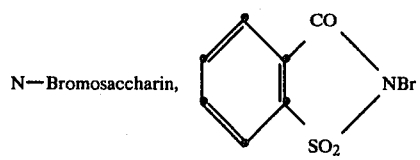

N—Bromo-N—phenylbenzenesulphonamide, C₆H₅SO₂NBrC₆H₅

N—Bromo-N,N—dibenzenesulphonamide, (C₆H₅SO₂)₂NBr

N—Bromosuccinimide, 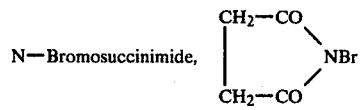

N—Bromo(perfluorosuccinimide), 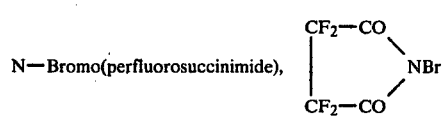

N—Bromoglutarimide, 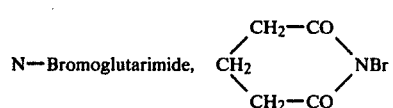

N—Bromophthalimide, 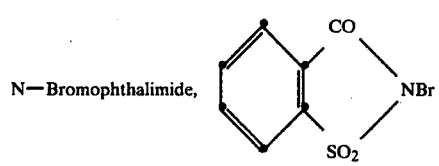

1-Bromo-5,5-dimethylhydantoin, 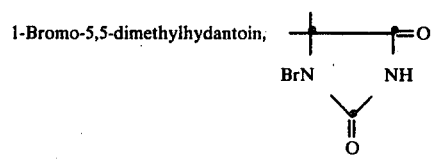

1,3-Dibromo-5,5-dimethylhydantoin, 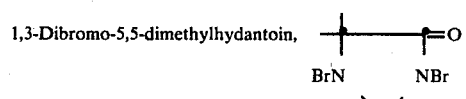

N,N—Dibromobarbituric acid, 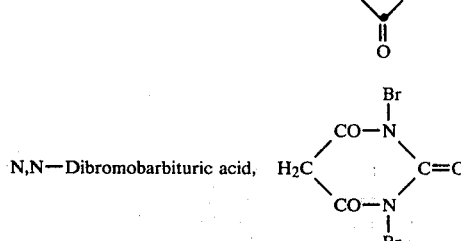

The O-bromo reagents preferably are the hypobromites, for example, sodium hypobromite, potassium hypobromite and calcium hypobromite.

Reagents suitable as sources of positive iodine are preferably the N-iodo reagents such as N-iodoimides such as N-iodosuccinimide, N-iodoglutarimide and N-iodophthalimide.

The starting materials employed in the process of this invention, namely, azetidin-2-one-4-sulfinic acids of the above formula 1, are known compounds and are described by Kukolja in U.S. Pat. No. 4,159,266. The azetidinone-4-sulfinic acids are prepared from the corresponding sulfinyl chlorides represented by the following formula

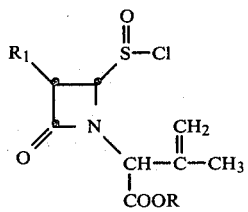

wherein $R_1$ and R have the same meanings as defined for formulas 1 and 2 hereinabove. The sulfinyl chloride is dissolved in a suitable water immiscible organic solvent such as ethyl acetate and the solution is slurried with an aqueous solution of sodium bicarbonate. The aqueous layer containing the sulfinic acid sodium salt is separated, washed with ethyl acetate and relayered with fresh ethyl acetate and then acidified. The organic layer containing the sulfinic acid is separated, washed and evaporated to dryness to provide the sulfinic acid as an amorphous solid.

The sodium salts of some of the sulfinic acids used in the invention are sufficiently soluble in ethyl acetate such that only minor amounts will partition into water as described above. In these instances the hydrolysis can be carried out using toluene or by the alternative acid hydrolysis described below.

Alternatively, the azetidinone sulfinyl chloride can be hydrolyzed in an aromatic hydrocarbon such as toluene with 1 N hydrochloric acid.

Examples of sulfinic acids useful as starting materials in the process of this invention are the following wherein the formal names are used:

p-nitrobenzyl 3-methyl-2-(2-oxo-4-sulfino-3-phenylacetamido-1-azetidinyl)-3-butenoate,
p-methoxybenzyl 3-methyl-2-(2-oxo-4-sulfino-3-phenoxyacetamido-1-azetidinyl)-3-butenoate,
diphenylmethyl 3-methyl-2-[2-oxo-4-sulfino-3-(4-methylbenzamido)-1-azetidinyl]-3-butenoate,
2,2,2-trichloroethyl 3-methyl-2-(2-oxo-4-sulfino-3-chloroacetamido-1-azetidinyl)-3-butenoate,
p-nitrobenzyl 3-methyl-2-[-2-oxo-4-sulfino-3-(4-nitrobenzyloxycarbonylamino)-1-azetidinyl]-3-butenoate,
2,2,2-trichloroethyl 3-methyl-2-[2-oxo-4-sulfino-3-(2-thienylacetamido)-1-azetidinyl]-3-butenoate,
diphenylmethyl 3-methyl-2-[2-oxo-4-sulfino-3-(2-p-methoxybenzyloxycarbonyl-2-phenylacetamido)-1-azetidinyl]-3-butenoate,
2-iodoethyl 3-methyl-2-(2-oxo-4-sulfino-3-benzamido-1-azetidinyl)-3-butenoate, and
p-methoxybenzyl 3-methyl-2-(2-oxo-4-sulfino-3-phthalimido-1-azetidinyl)-3-butenoate.

The azetidinone sulfinyl chlorides which on hydrolysis form the corresponding sulfinic acids as described above are prepared as described by Kukolja, U.S. Pat. No. 4,081,440.

In carrying out the process of this invention a 3-acylamido- or 3-diacylamidoazetidin-2-one-4-sulfinic acid of the formula 1 is reacted in an inert organic solvent with one molar equivalent of the positive halogen reagent at a temperature between about −20° C. and about 45° C. The reaction proceeds rapidly and can be characterized as a desulfonation whereby the sulfinic acid group is displaced by a chloro, bromo or iodo group. With a positive chlorine reagent such as the preferred N-chlorosuccinimide, the reaction proceeds rapidly at a temperature of about 20° C. to 25° C. With a positive iodine or bromine reagent the reaction proceeds rapidly at lower temperatures of about −5° C. to about 5° C.

Inert organic solvents which can be used are those solvents which do not react appreciably either with the reactants or the 4-haloazetidinone products. Suitable solvents are the halogenated hydrocarbons such as methylene chloride, ethylene dichloride, 1,1,2-trichloroethane, ethylene dibromide, chloroform, bromoform, chlorobenzene, bromobenzene, and like solvents. A preferred solvent is methylene chloride.

After the reaction is complete, the 4-haloazetidinone product is best recovered by first washing the reaction mixture with water and brine. The washed mixture is dried and then evaporated to remove the solvent. The 4-haloazetidinone is obtained crystalline or as an amorphous solid.

Although, as described above, the azetidinone-4-sulfinic acid starting material can be isolated from the hydrolysis mixture of the corresponding sulfinyl chloride, the process of this invention can be carried out without isolating the sulfinic acid. As described in U.S. Pat. No. 4,081,440, the sulfinyl chloride is prepared by reacting a penicillin sulfoxide ester with a positive chlorine reagent such as an N-chloroimide, eg. N-chlorophthalimide. In general, the sulfinyl chlorides used to prepare the sulfinic acids (formula 1) are prepared by reacting the penicillin sulfoxide ester with 1.1 molar equivalents of N-chlorosuccinimide in a dry inert organic solvent, usually 1,1,2-trichloroethane or toluene, at a temperature of about 20° C. to about 120° C. As noted above, the sulfinyl chloride can be hydrolyzed to the sulfinic acid following isolation or it can be hydrolyzed to the sulfinic acid in the reaction mixture. According to an alternative method for carrying out the process of this invention, the sulfinyl chloride generated from the penicillin sulfoxide ester can be hydrolyzed to the sulfinic acid without isolation with aqueous acid or aqueous base, and the sulfinic acid immediately treated in the mixture with the positive halogen reagent to form the 4-haloazetidinone. In this alternative procedure at least two molar equivalents of the positive halogen reagent are required. One equivalent is used in the known reaction with the penicillin sulfoxide to form the azetidinone sulfinyl halide, while the second is used according to the process of this invention following hydrolysis of the sulfinyl chloride to the sulfinic acid.

In this alternative procedure, the alkaline hypohalite positive halogen reagents are particularly useful. Following the preparation of the sulfinyl halide, the hypohalites function both to hydrolyze the sulfinyl halide and as the positive halogen reagent in the process of this invention. Typical aqueous alkaline hypohalite solutions which are useful for this purpose are the sodium or calcium hypochlorites, hypobromites, and hypoiodites.

In an example of the process of this invention carried out by the alternative procedure, p-nitrobenzyl 7-phenoxyacetamidopenicillinate sulfoxide in dry toluene is heated at the reflux temperature for about 1.5 hours with a molar excess of N-chlorosuccinimide in the presence of calcium oxide to form p-nitrobenzyl 3-methyl-2-(2-oxo-4-chlorosulfinyl-3-phenoxyacetamido-1-azetidinyl)-3-butenoate. The reaction mixture is cooled to ice-bath temperature and a saturated aqueous solution of sodium bicarbonate and a molar equivalent of N-chlorosuccinimide are added. The two-phase mixture is stirred vigorously for about one hour, the organic phase is separated, is washed with brine, dried and evaporated. The residue of p-nitrobenzyl 3-methyl-2-(2-oxo-4-chloro-3-phenoxyacetamido-1-azetidinyl)-3-butenoate is slurried or triturated with ethyl acetate or diethyl ether to provide the product in crystalline form.

Examples of 4-chlorosulfinylazetidinones which can be used in the alternative procedure of this process are represented by the following formula

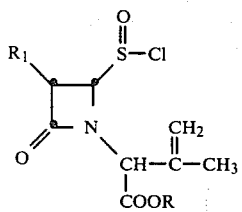

wherein $R_1$ and R are as follows:

| $R_1$ | R |
|---|---|
| phenoxyacetamido | p-nitrobenzyl |
| phenoxyacetamido | diphenylmethyl |
| phenoxyacetamido | p-methoxybenzyl |
| phenoxyacetamido | 2,2,2-trichloroethyl |
| phenylacetamido | diphenylmethyl |
| cyanoacetamido | benzyl |
| chloroacetamido | t-butyl |
| phthalimido | p-nitrobenzyl |
| succinimido | benzyl |
| 2-thienylacetamido | 2,2,2-trichloroethyl |
| 3-thienylacetamido | 2-iodoethyl |
| 2-furylacetamido | t-butyl |
| benzamido | diphenylmethyl |
| p-methylbenzamido | diphenylmethyl |
| p-chlorobenzamido | diphenylmethyl |
| acetamido | p-nitrobenzyl |
| 2-(p-methoxybenzyloxycarbonyl)-2-phenylacetamido | diphenylmethyl |
| p-chlorphenylthioacetamido | 2,2,2-trichloroethyl |
| p-chlorophenoxyacetamido | p-nitrobenzyl |
| 2-(t-butyloxycarbonylamino)-2-phenylacetamido | diphenylmethyl |
| 2-(tetrahydropyran-2-yl)-2-phenylacetamido | p-nitrobenzyl |

As mentioned above the 4-chlorosulfinylazetidinones are known compounds or can be obtained by the method described in U.S. Pat. No. 4,081,440, or as described by Chou in U.S. Pat. No. 4,075,203 using an epoxide or calcium oxide as a non-alkaline acid scavenger. Likewise, Chou describes the use of poly(4-vinylpyridine)-divinylbenzene copolymer crosslinked to about 2% as a preferred acid scavenger in the process for preparing the chlorosulfinylazetidinones with N-chloro halogenating agents, U.S. Pat. No. 4,190,724.

As described herein the process of the invention can be carried out with azetidinone-4-sulfinic acids or salts thereof with the 3-acylamido groups thereof in either the natural β-configuration or the epimeric α-form thereof. These α- and β-forms are depicted by the following partial formulas.

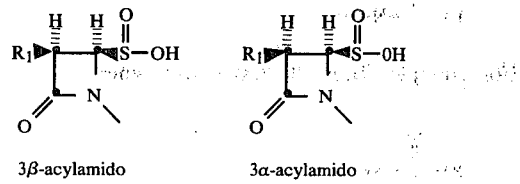

3β-acylamido      3α-acylamido

In the formulas 1 and 2 above the $R_1$ group is in either the α- or β-configuration and both are intended by the $R_1$- bonding as shown in the formulas herein, eg. formulas 1 and 2. The 4-haloazetidinones produced with the natural β-acylamido-4-sulfinic acids are obtained in different stereochemical forms depending upon the 4-halo atom. The 4-chloroazetidinones are obtained only as the cis-isomers of the following formula

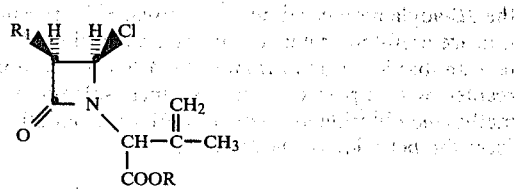

The 4-bromo and 4-iodoazetidinones are obtained as a mixture of the cis- and trans-isomers as represented by the following formulas wherein X is bromo or iodo.

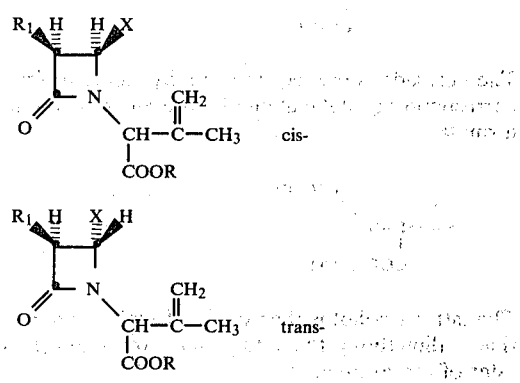

Attempts to separate these isomers of the 4-bromo and 4-iodoazetidinones via chromatography over silica gel yielded only the cis-isomer. It was found that in the presence of silica gel the trans-isomer was converted to the oxazoline compound represented by the following formula

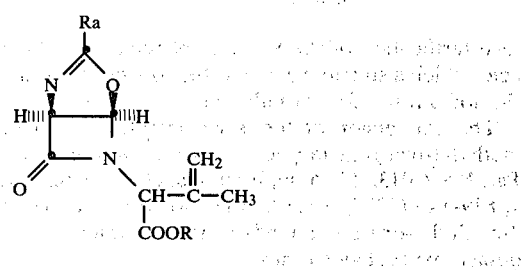

wherein R is a carboxy protecting group as defined hereinabove and Ra is the group $R_3$ derived from $R_1$ when $R_1$ is an amido group of the formula

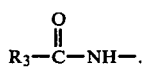

For example, Ra is phenoxymethyl when

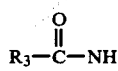

is phenoxyacetamido.

When $R_1$ of the formula 1 is an imido group, for example the phthalimido group, the oxazoline compound is not formed in the presence of silica gel with the trans-4-bromo or trans-4-iodo compound of the formula 2. Consequently, the trans 3-imido-4-bromo-(or 4-iodo)azetidin-2-ones (formula 2) can be separated from the cis-isomer and isolated by chromatography.

The 4-chloro, bromo, and iodoazetidinones having the 3β-acylamido configuration provided by this invention are useful intermediates in the preparation of β-lactam antibiotics. For example, the 4-haloazetidinone is reacted with a peroxy acid in an inert solvent such as methylene chloride at a temperature of about 20° C. to form the peroxide of the formula

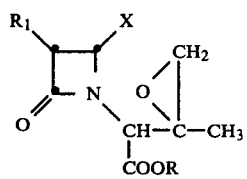

The peroxide is treated with triethylamine to form the corresponding allylic alcohol represented by the partial formula.

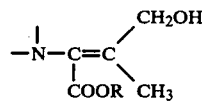

The latter alcohol is then cyclized with stannous chloride in dimethoxyethane to provide the 1-oxa-β-lactam ester of the formula.

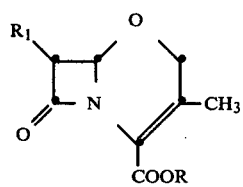

Deesterification of the R group provides the antibiotic acid which also may be converted to a salt form such as the sodium salt for formulation.

The conversion of the 4-haloazetidinones to the 3-methyl-1-oxa-β-lactam antibiotics is described in U.S. Pat. No. 4,013,653. Also, Narisada, et al., Heterocycles, 7, 839–849 (1977) describe the antibiotic activity of the 3-methyl-1-oxa compounds as greater than that of the desacetoxycephalosporins.

As described above the trans-4-bromo and trans-4-iodoazetidinones readily cyclize to form the oxazolines represented by the above structural formula. The oxazolines thus formed are useful intermediates in the preparation of 1-oxapenam antibiotics of the formula,

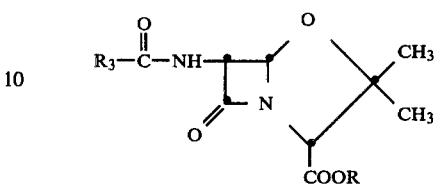

as described by U.S. Pat. Nos. 3,948,927 and 3,950,352 or according to U.S. Pat. No. 4,071,512.

As was mentioned above the 3β-acylamido-4-chloroazetidinone provided by the process of this invention is formed only as the cis-isomer. This isomer does not cyclize with silica gel to form the desired oxazoline. However, the cis-isomer (β-chloro) can be epimerized to the trans-isomer (α-chloro) by treating the cis-isomer with lithium chloride in acetone. The epimerization is illustrated below.

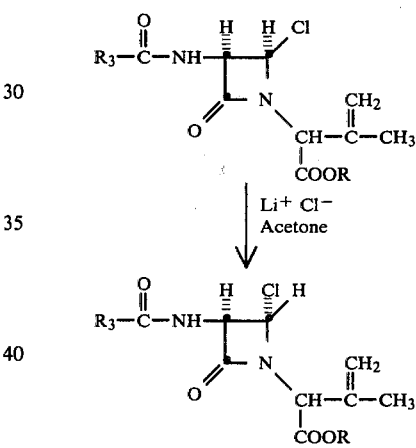

The trans epimerization product can be readily cyclized over silica gel to the desired oxazoline.

Alternatively, the cis-4-chloro-3β-acylamidoazetidinone obtained in the process of the invention can be converted to the desired oxazoline by the method described by Spitzer, et al., in U.S. Pat. No. 4,243,588. According to the process, a 3β-acylamido-4β-chloroazetidinone ester is reacted at a temperature between about 0° C. and about 60° C. in dimethylsulfoxide with between about 0.1 and about 2.0 molar equivalents of lead difluoride per mole of chloroazetidinone to provide the oxazoline as shown in the following scheme.

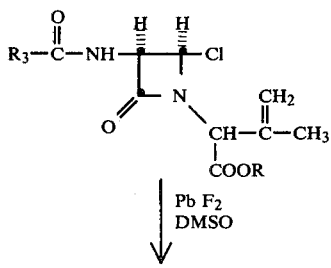

-continued

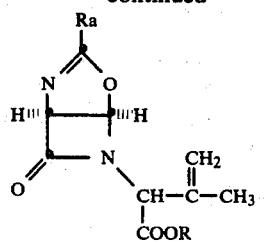

wherein R₃, Ra and R have the previously defined meanings.

The 3-epi-acylamidoazetidinone-4-sulfinic acids provide, on treatment with a positive chloro reagent, the trans-4-chloroazetidinone of the following partial formula.

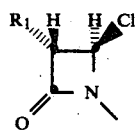

The 4-bromo and 4-iodo products formed with the epimeric 3-acylamidoazetidinone sulfinic acids or salts thereof are obtained in both the cis and trans forms as shown below.

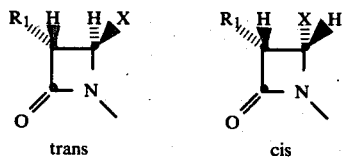

wherein X is bromo or iodo.

The 3-epi- or 3α-acylamido-4-haloazetidinones provided by the present invention wherein the 4-halo group has the β-configuration cyclize in the presence of silica gel, as in the case of the 3β-acylamido-4-haloazetidinones, to form the epi-oxazolines represented by the formula.

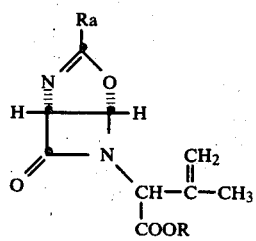

wherein Ra and R have the previously defined meanings.

The epi-oxazolines are useful intermediates in the preparation of 1-oxa-β-lactam antibiotics as described by S. Uyeo, et al., U.S. Pat. No. 4,233,216, particularly at columns 7 and 8.

In carrying out the process of this invention certain starting materials are preferred. 4-Sulfinic acids wherein R₁ is an acylamido group

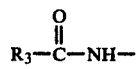

are preferred. Especially preferred R₃ groups are phenyl and substituted phenyl eg. p-tolyl and p-chlorophenyl. Also preferred are R₃=benzyl and phenoxymethyl.

Preferred R groups are p-nitrobenzyl, p-methoxybenzyl and diphenylmethyl.

Preferred positive chlorine reagents are N-chlorosuccinimide and N-chlorophthalimide, while calcium hypochlorite is also preferred.

Preferred positive bromine and iodine reagents are the N-bromo and N-iodosuccinimides and phthalimides.

In carrying out the process of the invention the preferred halogens are bromine and chlorine while chlorine because of its general versatility is most preferred.

The 4-haloazetidinones of this invention can be N-deacylated to provide the corresponding 3-amino-4-haloazetidinone ester. The deacylation is carried out by following the known two-step N-deacylation employed for the preparation of 7-amino cephalosporins, for example, as described by Fechtig, et al., U.S. Pat. No. 3,697,515. The reaction comprises forming an imino halide of the 3-position acylamido group with phosphorus pentachloride and conversion of the imino halide to an imino ether followed by hydrolysis or decomposition of the imino ether to the 3-amino-4-haloazetidinone. The process is carried out by reacting the 3-acylamido-4-haloazetidinone in a halogenated hydrocarbon solvent such as chloroform or methylene chloride with an excess of phosphorus pentachloride to form the corresponding imino chloride. The imino chloride formation is carried out at a temperature between about −20° C. and about 10° C. After imino chloride formation is completed, a lower alkanol, such as methyl alcohol or n-propyl alcohol is added to the cold reaction mixture to form the imino ether. Thereafter the reaction mixture is treated with water and the 3-amino-4-haloazetidinone is isolated as the hydrochloride salt.

The following reaction scheme illustrates the above described N-deacylation.

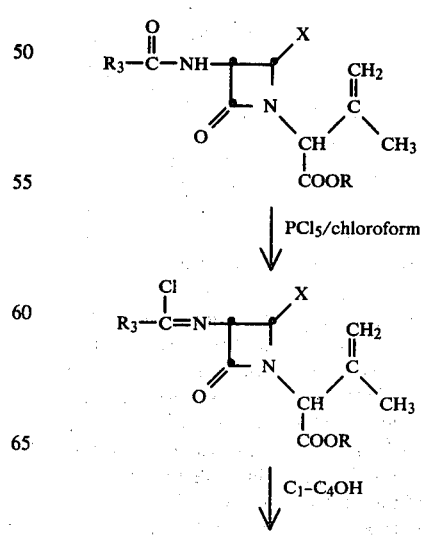

-continued

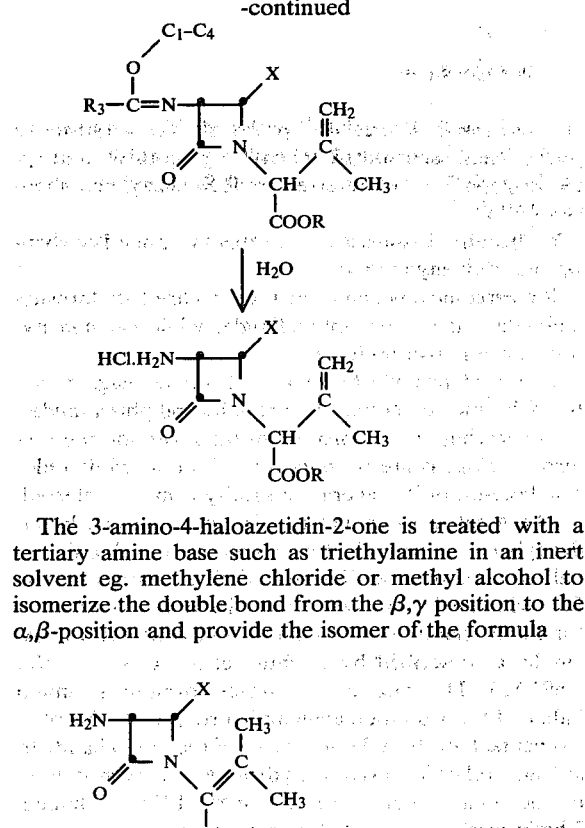

The 3-amino-4-haloazetidin-2-one is treated with a tertiary amine base such as triethylamine in an inert solvent eg. methylene chloride or methyl alcohol to isomerize the double bond from the β,γ position to the α,β-position and provide the isomer of the formula

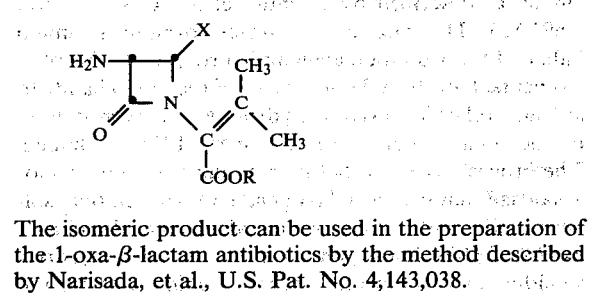

The isomeric product can be used in the preparation of the 1-oxa-β-lactam antibiotics by the method described by Narisada, et al., U.S. Pat. No. 4,143,038.

The following Examples further illustrate this invention.

EXAMPLE 1 p-Nitrobenzyl 3-methyl-2-(2-oxo-4-sulfino-3-phenoxyacetamido-1-azetidinyl)-3-butenoate A solution of 100 g. of p-nitrobenzyl 6-phenoxyacetamidopenicillinate sulfoxide in 3500 ml. of toluene containing in suspension 44 g. of calcium oxide was heated to the reflux temperature in a five-liter flask equipped with a stirrer, thermometer and a Dean-Stark trap. The mixture was refluxed until 100 ml. of toluene were collected in the trap. The heat was removed and 44 g. of N-chlorophthalimide and 30 ml. of butylene oxide were added. The reaction mixture was then heated at the reflux temperature for about one hour and forty minutes. The butylene oxide was distilled off with toluene and collected in the trap and the reaction mixture was then cooled to about 0° C. in an ice bath. The 4-chlorosulfinylazetidinone product was hydrolyzed in solution by adding one liter of 1 N hydrochloric acid with vigorous stirring of the two-phase mixture. After one hour of stirring, 300 ml. of acetone was added and the organic phase was washed three times with 500 ml-portions of brine. To the organic phase were added 400 ml. of distilled water and the pH was adjusted to 8 with sodium bicarbonate. The aqueous phase containing the azetidinone-4-sulfinic acid sodium salt was washed with ethyl acetate and then layered with 800 ml. of fresh ethyl acetate. The pH was adjusted to 2 with 1 N hydrochloric acid. The organic phase was separated, dried over magnesium sulfate and evaporated to dryness on a rotary evaporator. The azetidinone-4-sulfinic acid was obtained as a white foam in 50% yield.

NMR (CDCl$_3$): signals δ at 1.9 (s, 3H, CH$_3$), 4.46 (s, 2H, side chain CH$_2$), 4.88 (d, 1H, J=5.0 Hz, azet. H), 5.0 (s, 1H, CHCOOpNB), 5.2 (m, 2H, C$_2$=), 5.3 (s, 2H, CH$_2$ ester), 5.8 (dd, 1H, J=5.0 and 8.0 Hz), 16.–8.4 (m, 9H, aromatic H) and 8.4 (d, 1H, J=8.0 Hz NH).

EXAMPLE 2 p-Nitrobenzyl 3-methyl-2-(2-oxo-4-sulfino-3-phthalimido-1-azetidinyl)-3-butenoate A solution of 49.7 g. (0.1 mole) of p-nitrobenzyl 6-phthalimidopenicillinate sulfoxide and 13.4 g. (0.1 mole) of N-chlorophthalimide in 1.5 liters of 1,2-dichloroethane was heated at the reflux temperature for 70 minutes. After cooling, the reaction mixture was washed with water and brine, dried over magnesium sulfate and evaporated to dryness. There were obtained 52 g. of the azetidinone sulfinyl chloride.

NMR (CDCl$_3$): signal δ at 1.97 (s, 3H), 5.05 (s, 1H), 5.4 (s, 2H), 5.76 (d, 1H, J=5 Hz), 5.91 (d, 1H, J=5 Hz), and 7.83 (m, 8H, aromatic H).

The sulfinyl chloride was converted to the sulfinic acid by slurrying an ethyl acetate solution of the chloride with a 5% solution of sodium bicarbonate at room temperature for two hours. The aqueous layer was separated, washed with ethyl acetate, layered with fresh ethyl acetate, and acidified with hydrochloric acid. The ethyl acetate layer was separated, dried and evaporated to provide the azetidinone-4-sulfinic acid as a colorless foam.

NMR (CDCl$_3$): signals δ at 1.92 (s, 3H), 4.88 (s, 1H, J=4.5 Hz), 5.00 (s, 2H), 5.18 (broad s, 1H), 5.38 (s, 2H), 5.67 (d, 1H, J=4.5 Hz) and 7.5–8.3 (m, 9H, aromatic H).

EXAMPLE 3 p-Nitrobenzyl 3-methyl-2-(2-oxo-4-chloro-3-phenoxyacetamido-1-azetidinyl)-3-butenoate To a solution of 516 mg. (1 mmole) of p-nitrobenzyl 3-methyl-2-(2-oxo-4-sulfino-3-phenoxyacetamido-1-azetidinyl)-3-butenoate in 25 ml. of methylene chloride were added 140 mg. of N-chlorosuccinimide. A rapid reaction took place as shown by the exotherm. The reaction mixture was poured into 200 ml. of ethyl acetate and the solution was washed three times with 250 ml. portions of brine. The solution was dried over magnesium sulfate and evaporated to dryness on a rotary evaporator in vacuo to provide the cis-4-chloroazetidinone in about an 80% yield. The product after recrystallization from ethyl acetate melts at about 131°–132° C.

EXAMPLE 4

Diphenylmethyl 3-methyl-2-(2-oxo-4-chloro-3-phenoxyacetamido-1-azetidinyl)-3-butenoate A suspension of 20 g. of diphenylmethyl 6-phenoxyacetamidopenicillinate sulfoxide and 20 g. of calcium oxide in 700 ml. of toluene was heated at the reflux temperature in a reaction vessel equipped with a Dean-Stark trap. After 100 ml. of toluene were collected in the trap, heating was discontinued while 10 g. of N- chlorosuccinimide were added. The reaction mixture was reheated at the reflux temperature for 1.5 hours and then cooled in an ice bath. N-Chlorosuccinimide, 10 g., and 300 ml. of a saturated aqueous solution of sodium bicarbonate were added to the reaction mixture with stirring. After stirring for two hours the organic phase was separated, washed three times with brine, dried over magnesium sulfate and the solvent evaporated under vacuum in a rotary evaporator. A small amount of ether was added and the flask scratched to induce crystallization. There were obtained 12.2 g. of the crystalline cis-4-chloroazetidinone diphenylmethyl ester. On recrystallization from diethyl ether the product melts at about 71° C. to about 73° C.

EXAMPLE 5

Diphenylmethyl 3-methyl-2-(2-oxo-4-chloro-3-phenylacetamido-1-azetidinyl)-3-butenoate A suspension of 2.5 g. (4.8 mmole) of diphenylmethyl 6-phenylacetamidopenicillinate sulfoxide and 2.5 g. of calcium oxide in 125 ml. of toluene is heated at the reflux temperature in a reaction vessel equipped with a stirrer, thermometer, and a Dean-Stark trap. After about 25 ml. of toluene are collected in the trap heating is discontinued and 1.3 g. (9.7 mmoles) of N-chlorosuccinimide are added. The reaction mixture is heated at the reflux temperature for 1.5 hours and is then cooled in ice bath. About 50 ml. of a saturated aqueous solution of sodium bicarbonate is added and the mixture is stirred for 1.5 hours. The organic phase is separated, washed with brine, dried, and evaporated. The product is often obtained as a gum which can be crystallized if desired with ether or ethyl acetate.

EXAMPLE 6

Diphenylmethyl 3-methyl-2-(2-oxo-4-chloro-3-phenoxyacetamido-1-azetidinyl)-3-butenoate A suspension of 12.5 g. of poly-(4-vinylpyridine) divinylbenzene crosslinked copolymer (2% crosslinked) in one liter of toluene was heated at the reflux temperature while 150 ml. of toluene were distilled off with water. Heating was discontinued and 21.2 g. (40 mmole) of diphenylmethyl 6-phenoxyacetamidopenicillanate sulfoxide and 7.98 g. (44 mmole) of N-chlorophthalimide were added to the warm suspension. The reaction mixture was reheated at the reflux temperature for 100 min. after which the mixture was cooled to 10° C. and was stirred for 10 min. The insoluble copolymer and phthalimide were filtered and discarded. To the filtrate containing the azetidinone-4-sulfinyl chloride were added 10.72 g. (80 mmole) of N-chlorosuccinimide and 200 ml. of a saturated aqueous solution of sodium bicarbonate and the mixture vigorously stirred for one hour. The organic phase was separated, washed 3 times with brine, dried over magnesium sulfate, and evaporated to dryness under reduced pressure. The reaction product obtained as a gum was dissolved in 50 ml. of diethyl ether. After standing for 15 min. at room temperature and after scratching the flask to induce crystallization the product crystallized from solution. The product was filtered and washed three times with diethyl ether. There were obtained 10.1 g. of the title compound.

EXAMPLE 7 p-Nitrobenzyl 3-methyl-2-(2-oxo-4-bromo-3-phenoxyacetamido-1-azetidinyl)-3-butenoate A solution of 517 mg. (1 mmole) of p-nitrobenzyl 3-methyl-2-(2-oxo-4-sulfino-3-phenoxyacetamido-1-azetidinyl)-3-butenoate in 50 ml. of methylene chloride was cooled to 0° C. and 0.178 g. (1 mmole) of N-bromosuccinimide were added. After 5 minutes the reaction mixture was washed with brine, dried, and evaporated under vacuum in a rotary evaporator. The 4-bromoazetidinine product was obtained as a solid residue whose nmr spectrum showed the product was a mixture of the cis- and trans-isomers.

Chromatography of the product provided the cis-4-bromoazetidinone.

NMR (CDCl$_3$) signals δ at 1.96 (s, 3H, CH$_3$), 4.58 (s, 2H, CH$_2$-O-phenyl), 4.83 (s, 1H, CHCOOpNB), 5.05–5.2 (m, 2H, CH$_2$=), 5.7 (dd, 1H, J=5.0 Hz, azet. H), 6.3 (d, 1H, J=5.0 Hz, azet. H), and 6.9–8.3 (m, 10H, aromatic H and NH).

The trans-4-bromoazetidinone was converted during the chromatography to the oxazolineazetidinone represented by the formula

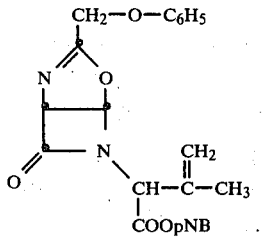

EXAMPLE 8 p-Nitrobenzyl 3-methyl-2-(2-oxo-4-iodo-3-phenoxyacetamido-1-azetidinyl)-3-butenoate A solution of p-nitrobenzyl 3-methyl-2-(2-oxo-4-sulfino-3-phenoxyacetamido-1-azetidinyl)-3-butenoate in methylene chloride was cooled to 0° C. and one molar equivalent of N-iodosuccinimide was added with stirring. After 5 minutes the reaction mixture was washed with brine, dried and evaporated. The product obtained as a solid residue was shown by its nmr spectrum to contain about a 2:1 ratio of cis-isomer to trans-isomer contaminated with a trace of oxazolineazetidinone.

EXAMPLE 9 p-Nitrobenzyl 3-methyl-(2-oxo-4-chloro-3-phenoxyacetamido-1-azetidinyl)-3-butenoate Toluene (700 ml.) and 20 g. of penicillin V sulfoxide p-nitrobenzyl ester were placed in a reaction vessel equipped with a thermometer, stirrer and a Dean-Stark trap. The mixture was heated at the reflux temperature until about 100 ml. of toluene were collected in the trap. Heating was discontinued while 16 g. of N-chlorosuccinimide were added and then continued for 1.5 hours at the reflux temperature. The reaction mixture was cooled in an ice bath and a 5% solution of sodium hypochlorite was added. The mixture was stirred for two hours and the organic phase was separated, washed with brine, dried and evaporated. There were obtained 13.3 g. (68%) of the crystalline 4- chloroazetidinone ester.

EXAMPLE 10

2,2,2-Trichloroethyl 3-methyl-2-[2-oxo-4-chloro-3-(2-thienylacetamido)-1-azetidinyl]-3-butenoate A solution of 3.5 g. (7.5 mmole) of 6-(2-thienylacetamido)penicillanic acid sulfoxide 2,2,2-trichloroethyl ester in 350 ml. of toluene was heated at the reflux temperature while about 100 ml. of toluene were collected in a Dean-Stark trap. Heating was discontinued while 1 g. (7.5 mmole) of N-chlorosuccinimide were added. Heating was continued at the reflux temperature for 50 minutes after which the reaction was a light orange color. The reaction mixture containing the 4-chlorosulfinylazetidinone was cooled and treated with a large excess of a 5% solution of sodium hypochlorite for one hour. The organic phase was separated, washed with brine, dried and evaporated to dryness. The solid residue of product was purified via silica gel preparative thin layer chromatography and the cis-4-chloroazetidinone was obtained on elution.

EXAMPLE 11

2,2,2-Trichloroethyl 3-methyl-2-[2-oxo-4-chloro-3-(p-nitrobenzyloxycarbonylamino)-1-azetidinyl]-3-butenoate Toluene, 150 ml., and 10 mmole of 2,2,2-trichloroethyl 6-(p-nitrobenzyloxycarbonylamino)penicillanate sulfoxide were heated at the reflux temperature in a flask equipped with a Dean-Stark trap until 20 ml. of toluene were collected. Heating was discontinued while two equivalents of N-chlorosuccinimide were added and then continued for 1.5 hours. The reaction mixture was cooled in an ice bath. One equivalent of N-chlorosuccinimide and 30 ml. of aqueous saturated solution of sodium bicarbonate were added with stirring. The mixture was stirred overnight, the organic layer was separated, washed with an additional portion of sodium bicarbonate solution and dried (MGSO4). The solvent was evaporated under vacuum in a rotary evaporator providing the crude product as a solid residue. The nmr of the product showed the major factor to be the cis-4-chloroazetidinone ester.

EXAMPLE 12 p-Nitrobenzyl 3-methyl-2-(2-oxo-4-chloro-3-epi-phenoxyacetamido-1-azetidinyl)-3-butenoate A. Preparation of p-nitrobenzyl 3-methyl-2-(2-oxo-4-sulfino-3-epi-phenoxyacetamido-1-azetidinyl)-3-butenoate A suspension of 20 g. of poly(4-vinylpyridine)divinylbenzene, crossed linked at about two percent, in 1300 ml. of toluene in a round bottomed, 3-necked flask equipped with a stirrer, thermometer, reflux condenser and a Dean-Stark trap was heated at the reflux temperature (ca. 110° C.) until all water was distilled out and collected in the trap with toluene. Heating was discontinued, 10 g. (20 mmole) of p-nitrobenzyl 6-epi-phenoxyacetamidopenicillinate sulfoxide and 2.6 g. (1 eg.) of N-chlorosuccinimide were added, and the mixture reheated at the reflux temperature for 20 min. The reaction mixture was cooled in an ice bath and was filtered to remove polymer and succinimide. The filtrate containing the 4-chlorosulfinyl product was added to 600 ml. of 1 N hydrochloric acid containing 200 ml. of acetone. The hydrolysis mixture was stirred in the cold for one hour. The 3-epi-phenoxyacetamidoazetidinone-4-sulfinic acid was recovered by extracting the organic phase with aqueous sodium bicarbonate and acidifying the extract while slurrying in ethyl acetate. The ethyl acetate was separated, dried over magnesium sulfate and evaporated to dryness. There were obtained 2.3 g. of the 3-epi-azetidinone-4-sulfinic acid.

B. Preparation of title compound

To a solution of 600 mg. of the p-nitrobenzyl 3-methyl-2-(2-oxo-4-sulfino-3-epi-phenoxyacetamido-1-azetidinyl)-3-butenoate (Part A) in 20 ml. of chloroform were added 160 mg (1 eq.) of N-chlorosuccinimide. The mixture was stirred for about 10 min., was washed with brine, dried and evaporated on a rotary evaporator under vacuum. A nearly quantitative yield of the 4-chloroazetidinone ester was obtained.

EXAMPLE 13 p-Nitrobenzyl 3-methyl-2-(2-oxo-4-chloro-3-amino-1-azetidinyl)-3-butenoate

To a solution of 5 mmoles of p-nitrobenzyl 3-methyl-2-(2-oxo-4-chloro-3-phenoxyacetamido-1-azetidinyl)-3--butenoate in 20 ml. of chloroform cooled to −10° C. were added 30 mmoles of phosphorus pentachloride and an excess of quinoline (30 mmoles plus). The reaction mixture was stirred for 30 min. and was then cooled to −30° C. To the cold mixture were added 2 ml. of n-propyl alcohol with stirring and the reaction mixture was allowed to stand in an ice bath for about 3 min. Thereafter 5 ml. of a saturated aqueous solution of sodium chloride were added followed by the addition of 100 ml. of petroleum ether. The product precipitated as a gum from which the liquid phase was decanted. The gum solidified on treatment with 5 ml. of saturated aqueous sodium chloride. The product was filtered and dried. There were obtained 400 mg. of the deacylated product as the hydrochloride salt represented by the following formula.

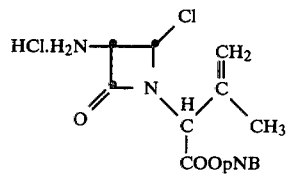

wherein pNB=p-nitrobenzyl.

EXAMPLE 14

Isomerization of p-nitrobenzyl 3-methyl-2-(2-oxo-cis-4-chloro-3-phenoxyacetamido-1-azetidinyl)-3-butenoate To a solution of 300 mg. of the 4-chloroazetidinone, cis-isomer, prepared according to the process of this invention in 150 ml. of acetone was added a spatula full of lithium chloride and the mixture was stirred for one hour at room temperature. The trans-4-chloroazetidinone formed was recovered as follows. The reaction mixture was diluted with ethyl acetate and washed with a saturated aqueous solution of sodium chloride. The organic phase was separated, dried, and evaporated to dryness under reduced pressure to provide a solid residue whose nuclear magnetic resonance spectrum showed a mixture of cis- and trans-4-chloroazetidinone esters.

We claim:

1. A process for preparing a 4-haloazetidinone of the formula

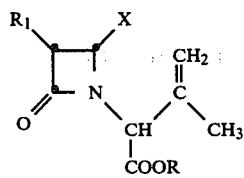

which comprises reacting in an inert solvent at a temperature between about −20° C. and about 45° C. a 4-sulfinoazetidinone of the formula

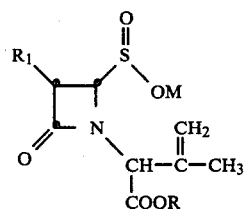

with at least one molar equivalent of an N-X or O-X positive halogen reagent, where in the above formulas M is hydrogen, sodium or potassium, X is chloro, bromo, or iodo; R is a carboxy-protecting group; and $R_1$ is (1) an imido group of the formula

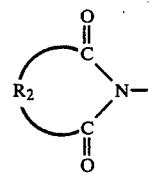

wherein $R_2$ is $C_2$–$C_4$ alkenylene or 1,2-phenylene;

(2) an amido group of the formula

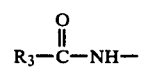

wherein $R_3$ is (a) hydrogen, $C_1$–$C_4$ alkyl, halomethyl, cyanomethyl, benzyloxy, p-nitrobenzyloxy, t-butyloxy, 2,2,2-trichloroethoxy, or p-methoxybenzyloxy;

(b) the group R', wherein R' is phenyl or phenyl substituted by 1 or 2 halogens, protected hydroxy, nitro, cyano, $C_1$–$C_4$ alkyl, or $C_1$–$C_4$ alkoxy;

(c) a group of the formula

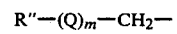

wherein R" is R' as defined above, 1,4-cyclohexadienyl, thienyl or furyl; m is 0 or 1; and Q is O or S; with the limitation that when m is 1, R" is R';

(d) a group of the formula

wherein R" is as defined above, and W is protected hydroxy, protected carboxy, or protected amino;

(3) an imidazolidinyl group of the formula

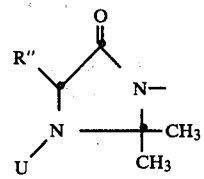

wherein R" is as defined above and U is nitroso or acetyl; or $R_1$ is (4) an imido group of the formula

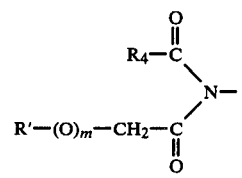

wherein R' is as defined above, m is 0 or 1, and $R_4$ is $C_1$–$C_4$ alkyl, $C_1$–$C_4$ haloalkyl, $C_1$–$C_4$ alkoxy, or 2,2,2-trichloroethoxy.

2. The process of claim 1 wherein $R_1$ is an amido group of the formula

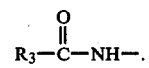

3. The process of claim 2 wherein $R_3$ is phenyl or substituted phenyl.

4. The process of claim 2 wherein $R^3$ is a group of the formula

5. The process of claim 4 wherein R" is R'.

6. The process of claim 5 wherein $R_3$ is phenoxymethyl.

7. The process of claim 1 wherein $R_1$ is an imido group of the formula

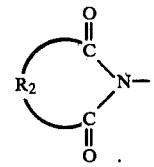

8. The process of claim 7 wherein $R_1$ is phthalimido.

9. The process of claim 1 wherein X is chloro.

10. The process of claim 9 wherein the positive chlorine reagent is an N-chloro compound.

11. The process of claim 10 wherein the N-chloro compound is N-chlorosuccinimide or N-chlorophthalimide.

12. The process of claim 9 wherein the positive chlorine reagent is hypochlorite.

13. The process of claim 1 wherein X is bromo.

14. The process of claim 13 wherein the positive bromine reagent is an N-bromo compound.

15. The process of claim 14 wherein the N-bromo compound is N-bromosuccinimide or N-bromophthalimide.

16. The process of claim 13 wherein the positive bromine reagent is hypobromite.

17. The process of claim 1 wherein X is iodo.

18. The process of claim 17 wherein the positive iodine reagent is N-iodosuccinimide.

19. The process of claim 9 or claim 13 wherein $R_1$ is phenoxyacetamido or phenylacetamido and R is p-nitrobenzyl or diphenylmethyl.

20. The process of claim 1 wherein $R_1$ is

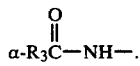

21. The process of claim 1 wherein R is

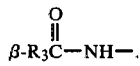

* * * * *